(12) United States Patent
Fueda

(10) Patent No.: US 7,772,215 B2
(45) Date of Patent: Aug. 10, 2010

(54) WATER DETECTION COMPOSITION AND WATER DETECTION INDICATOR

(75) Inventor: Yoshiyuki Fueda, Hyuga (JP)

(73) Assignee: Fuji Silysia Chemical Ltd., Aichi-Ken (JP)

(*) Notice: Subject to any disclaimer, the term of this patent is extended or adjusted under 35 U.S.C. 154(b) by 695 days.

(21) Appl. No.: 11/436,220

(22) Filed: May 18, 2006

(65) Prior Publication Data

US 2006/0270047 A1 Nov. 30, 2006

(30) Foreign Application Priority Data

May 31, 2005 (JP) ............... 2005-159815
Nov. 18, 2005 (JP) ............... 2005-334203

(51) Int. Cl.
*A01N 57/08* (2006.01)

(52) U.S. Cl. ........................ 514/79; 514/138

(58) Field of Classification Search ........... 540/145
See application file for complete search history.

(56) References Cited

U.S. PATENT DOCUMENTS

| | | | | |
|---|---|---|---|---|
| 5,281,616 | A * | 1/1994 | Dixon et al. | 540/145 |
| 6,455,320 | B1 | 9/2002 | Danz et al. | |
| 2003/0211618 | A1* | 11/2003 | Patel | 436/38 |
| 2005/0201893 | A1* | 9/2005 | Arno et al. | 422/58 |

FOREIGN PATENT DOCUMENTS

| | | |
|---|---|---|
| AU | 2004202709 A1 | 6/2004 |
| CN | 1473009 | 2/2004 |
| DE | 43 32 512 A1 | 3/1995 |
| DE | 4332512 | 3/1995 |

| | | |
|---|---|---|
| WO | 02/21948 | 3/2002 |

OTHER PUBLICATIONS

Groves et al. "Preparation and Characterization of a Dialkoxyiron (IV) Porphyrin", 1985, Journal of the American Chemical Society, 107, 354-360.*
Shamsipur et al. "Perchlorate selective membrane electrodes based on a phosphorous(V)-tetraphenylporphyrin complex". 2003, Sensors and Actuators B, 89, 9-14.*
"Test Method for Silica Gel JIS K 1150-1994", Japan Industrial Standard Committee Deliberation, pub.: Japan Standards Association, "5.13 Indicator Range of Blue Gel"; Aug. 1, 1994.

* cited by examiner

*Primary Examiner*—James O Wilson
*Assistant Examiner*—Brian McDowell
(74) *Attorney, Agent, or Firm*—Davis & Bujold, P.L.C.

(57) ABSTRACT

A novel water detection composition for use in place of blue gel and a water detection indicator. The water detection composition comprises, as active components, a porphyrin complex, and at least one inorganic acid salt of a metal selected from a group consisting of alkali metals, alkaline earth metals, Al and Fe. The porphyrin complex is:

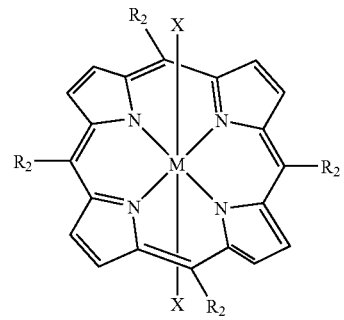

wherein M is P, X is selected from a group consisting of a halogen and OH, and $R_2$ is phenyl, and the water detection composition is supported by a silica gel.

2 Claims, 4 Drawing Sheets

WATER DETECTION COMPOSITION AND WATER DETECTION INDICATOR

BACKGROUND OF THE INVENTION (i) Field of the Invention

The present invention relates to a water detection composition and a water detection indicator.

(ii) Background Art

Silica gel impregnated with cobalt chloride is a known moisture indicator used for indicating the rate of moisture adsorption (water adsorption) (as shown, for example, in "Test Method for Silica Gel JIS K 1150-1994", established on Aug. 1, 1994, Japan Industrial Standard Committee Deliberation, Published by Japan Standards Association, "5.13 Indicator Range of Blue Gel"). Such cobalt chloride impregnated silica gel is generally called "blue gel" and is popularly used as a moisture indicator.

Since the known "blue gel", however, is not usable for all purposes, a market demand for a new moisture indicator in place of the blue gel has been increasing.

SUMMARY OF THE INVENTION

As a result of a keen examination to satisfy the market demand, the inventor of the present invention found that a composition containing a specific porphyrin complex and a specific inorganic acid salt sensitively changes the color according to changes in moisture.

The present invention, which has been devised based on the above finding, has an object to provide a novel water detection composition for use in place of blue gel and a water detection indicator by using the water detection composition.

To attain the above object, there is provided a water detection composition which comprises, as effective components: a porphyrin complex indicated by a general equation [I] as below (M is an element selected from a group consisting of Mg, Al, Si, P, Ca, Sc, Ti, V, Cr, Mn, Fe, Co, Ni, Cu, Zn, Ga, Ge, As, Mo, Ru, Rh, Pd, Ag, Cd, In, Sn, Sb, W, Re, Pt, Au, Hg, Tl, Pb, and Bi; X is a halogen or an OR, ($R_1$ is a hydrogen or an optional substituent replaceable with the hydrogen); and $R_2$ is a hydrogen or an optional substituent replaceable with the hydrogen); and at least one inorganic acid salt of a metal selected from a group consisting of alkali metals, alkaline earth metals, Al and Fe.

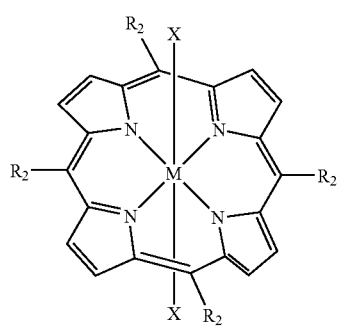

[I]

In the general equation [I], a central element M of the complex may be an element selected from Mg, Al, Si, P, Ca, Sc, Ti, V, Cr, Mn, Fe, Co, Ni, Cu, Zn, Ga, Ge, As, Mo, Ru, Rh, Pd, Ag, Cd, In, Sn, Sb, W, Re, Pt, Au, Hg, Tl, Pb, and Bi. The central element may be an ion. In this case, the complex indicated by the general equation [I] is a complex ion, which may be contained as a complex salt in the water detection composition. A coexistent ion to form the complex salt is preferably, for example, a halogen ion, such as $Br^-$, $Cl^-$ or $F^-$, or $OH^-$ although other ions may be employed.

X in the general equation [I] is a halogen (for example, Br, Cl, F, etc.) or an $OR_1$. When X is $OR_1$, $R_1$ is a hydrogen or an optional substituent replaceable with the hydrogen. The constituent may be any group which does not interfere with the action of a water detection composition. The constituent, however, is preferably a hydrogen, an alkyl group which may be replaced by a phenyl group, a cycloalkyl group, a phenyl group which may have a substituent, or an acyl group which may have a substituent, considering easiness in production, stability, etc. of the complex.

It is particularly preferable to employ hydrogen as $R_1$ and thus a hydroxy group as $-OR_1$, since the complex may be more stabilized on a support having a hydroxy group, such as silica gel. Examples of a substituent in "a phenyl group which may have a substituent or an acyl group which may have a substituent" are an alkyl group, an alkoxy group, a carboxy group, a fluoro group, a chloro group, a bromo group, an iodo group, a hydroxy group, a cyano group, an amino group, a formyl group, a phenyl group, an acyl group, and a nitro group.

$R_2$ in the general equation [I] is also a hydrogen or an optional substituent replaceable with the hydrogen. The constituent may be any group which does not interfere with the action of a water detection composition. The constituent, however, is preferably a phenyl group which may have a substituent, considering easiness in production, stability, etc. of the complex. The substituent which the phenyl group may have is, for example, an alkyl group, an alkoxy group, a carboxy group, a fluoro group, a chloro group, a bromo group, an iodo group, a hydroxy group, a cyano group, an amino group, a formyl group, a phenyl group, an acyl group, and a nitro group.

An inorganic acid to obtain at least one inorganic acid salt of a metal selected from a group consisting of "alkali metals, alkaline earth metals, Al and Fe" may be hydrochloric acid, sulfuric acid or nitric acid. It is preferable to employ hydrochloric acid or sulfuric acid which is more likely to cause substantial changes in color due to moisture adsorption as compared with nitric acid. Also, it is preferable to employ Ca or Mg, which is more likely to cause substantial changes in color due to moisture adsorption, among "alkali metals, alkaline earth metals, Al and Fe".

According to the water detection composition of the present invention constituted as above, changes in color are caused due to moisture adsorption or contact with water. It may, therefore, be possible to constitute a moisture indicator by using the water detection composition supported by a moisture-adsorbing support. It may also be possible to constitute a water leakage indicator by using the water detection composition supported by a water-adsorbing support.

It is difficult to exactly specify a required level of moisture-adsorbing property or water-adsorbing property for the support used for constituting the moisture indicator or the water leakage indicator (hereinafter generally referred to as the "water detection indicator") since the level should vary depending on a humidity to be detected and a state of water (water vapor, water). However, in a preferable specific example of the moisture indicator, a support preferably has a hygroscopicity of 0.1% or more at a relative humidity of 20%, 0.3% or more at a relative humidity of 50% and 1.0% or more at a relative humidity of 90%, according to "JIS Z0701 4.1 Hygroscopicity Test". It is more preferable to employ an inorganic porous support, and particularly preferable to employ a colorless support such as silica gel, which facilitates observation of changes in color due to moisture adsorption.

The above silica gel may be formed as a granular material. Alternatively, it may be possible to constitute a moisture-adsorbing support by impregnating or coating paper or another support with a fluid composition containing the above silica gel.

Concerning blue gel as a known moisture indicator, cobalt and cobalt compounds have recently been classified as a "Class 1 Designated Chemical Substance" according to The Law of Pollutant Release and Transfer Register". This leads to an increasing demand for safer substances in place of cobalt chloride.

In this respect, cobalt or an element other than cobalt may be selected as the central element of the complex according to the water detection composition in the present invention. It may, therefore, be possible to avoid such a "Class 1 Designated Chemical Substance" and employ a safer element in accordance with the intended use, and thus provide a water detection indicator which will cause less adverse effects on human health and the ecosystem.

BRIEF DESCRIPTION OF THE DRAWINGS

Preferred embodiments of the present invention will be described hereinafter with reference to the drawings, in which.

DETAILED DESCRIPTION OF THE PREFERRED EMBODIMENTS

First Embodiment

Figure 1:
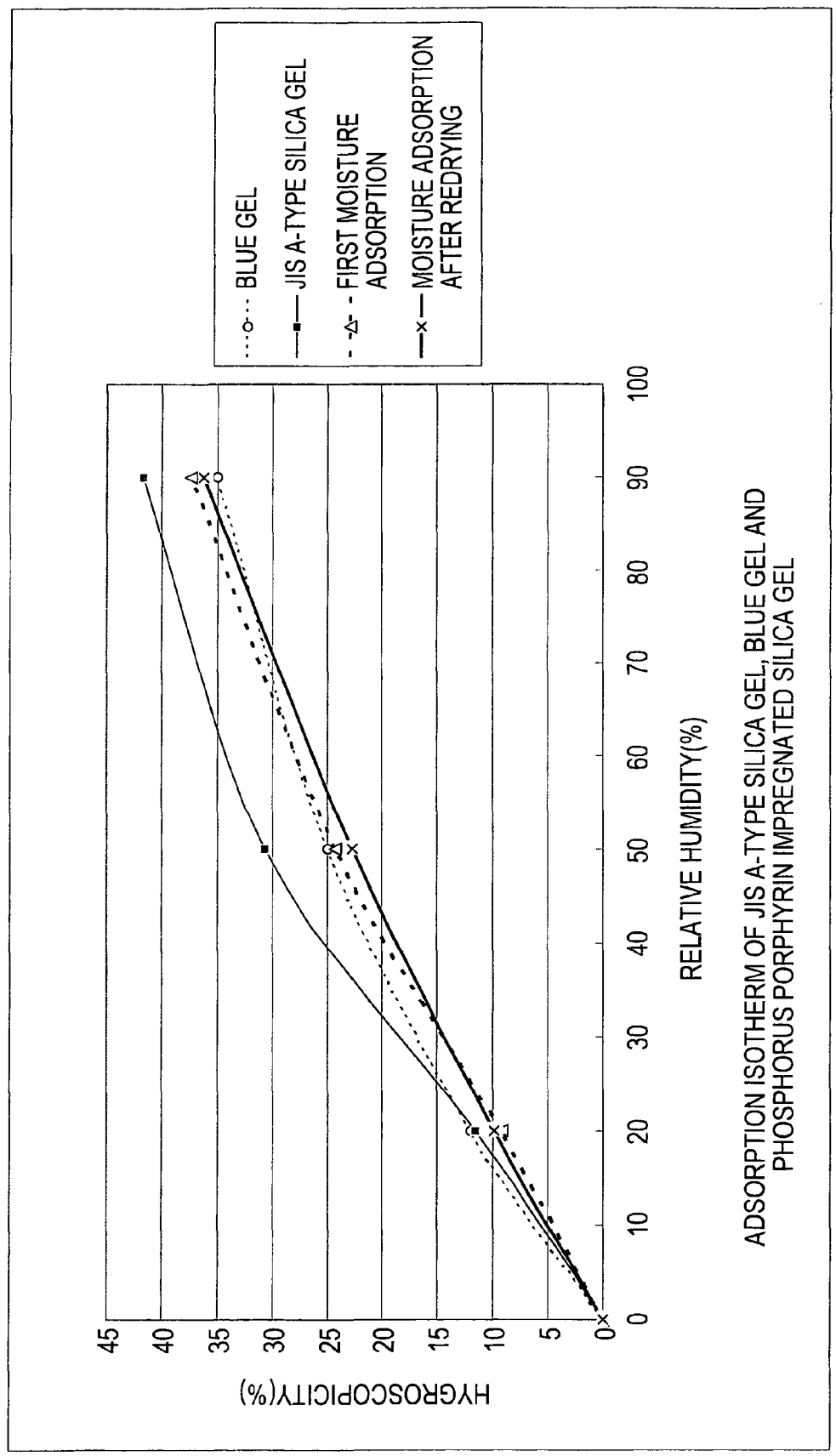
FIG. 1 is a graph showing an adsorption isotherm of a sample in a second embodiment.

First, a phosphorus porphyrin was synthesized according to the following procedure.

A reflux apparatus was provided to a glass reaction vessel of 50 L. In the reaction vessel, tetra-phenyl porphyrin ($H_2$TTP: 120 g) was dissolved into 12 L of dehydrated pyridine in a nitrogen gas stream, and 2.4 L of $POCl_3$ was added to prepare a reaction solution.

Then, the reaction solution was adequately refluxed, while the reaction was monitored by a UV-vis spectrum. When a shift of a Soret absorption band from 416 nm to 438 nm was confirmed, the reaction was terminated. After the termination of the reaction, the reaction vessel was left to cool down to the room temperature.

Subsequently, 120 L of hexane was placed in a glass vessel of 500 L, and the reaction solution after the termination of the reaction was added by drops for about 1 hour while stirring the hexane to cause reprecipitation. The precipitate was adequately dissolved in 36 L of chloroform for about 30 minutes.

Furthermore, 80 L of de-ionized water was added to the chloroform solution to remove inorganic salt, and the mixture was stirred for 30 minutes. Then, the mixture was left standing for about 30 minutes to be separated into two layers. The pH of a water layer was determined, and then the water layer was discarded. This process was further repeated twice to adequately wash the chloroform layer with water.

The chloroform layer was evaporated to dryness by an evaporator under vacuum, and was further dried for 2 to 3 days under vacuum by a vacuum pump. There was thus obtained a phosphorus porphyrin complex with two chlorine atoms as axial ligands ([P(V)TPP(Cl)$_2$]Cl; hereinafter referred to as "phosphorus porphyrin complex (A)"). The yield was 92%.

The phosphorus porphyrin complex (A) synthesized according to the above procedure is a chemical compound indicated by a chemical formula [II] as below.

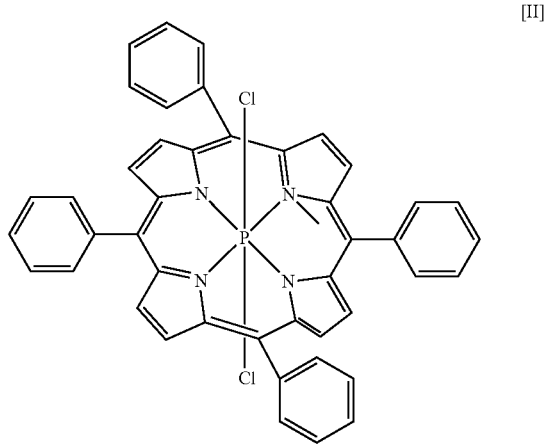

[II]

Subsequently, 1.0 g of the phosphorus porphyrin complex (A) was dissolved in 160 ml of acetonitrile solution containing 25% of water and was refluxed for 1 hour in the air, in order to replace the axial ligands with hydroxy groups. The reaction was monitored by a UV-vis spectrum. When a shift of a Soret absorption band from 438 nm to 423 nm was confirmed, the reaction was terminated.

After the acetonitrile solution was condensed to about 40 ml by an evaporator, chloroform was added to separate the mixture into two layers. A chloroform layer was separately removed, and reduced pressure distillation of a solvent was performed. There was thus obtained a target compound, i.e., a phosphorus porphyrin complex with hydroxy groups as two axial ligands ([P(V)TPP(OH)$_2$]Cl; hereinafter referred to as "phosphorus porphyrin complex (B)"). The yield was 99%.

The phosphorus porphyrin complex (B) synthesized according to the above procedure is a chemical compound indicated by a chemical formula [III] as below.

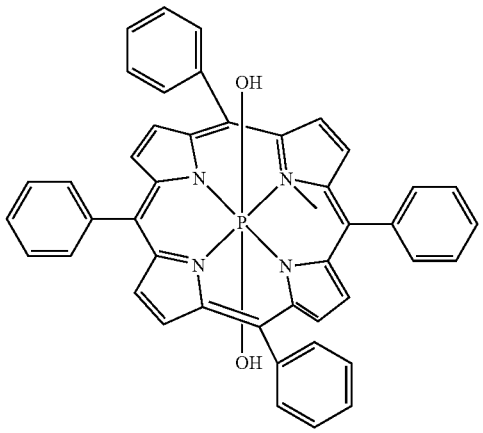

[III]

Subsequently, 0.42 g of the phosphorus porphyrin complex (B) was dissolved in 1 L of methanol, then mixed into 4 L of toluene and stirred. Then, 1 kg of silica gel (specific surface area: 280 m²/g, pore volume: 1.0 ml/g, particle size: 1.70-4.00 mm) was added, and then the mixture was left standing overnight with occasional stirring.

Subsequently, the mixture was distilled with a distillation apparatus to evaporate methanol. The mixture was refluxed for 3 hours after the evaporation of methanol, left to cool down, and deliquored. Then, a residue was dried.

Obtained phosphorus porphyrin impregnated silica gel was put in a 1 weight % calcium chloride solution. Then, the solution was drained, and a residue was dried at a temperature of 100 C.° to obtain a sample. In this case, an added amount of phosphorus porphyrin was 420 μg and an added amount of calcium chloride was 0.01 g per 1 g of the silica gel.

It was observed that the color of the obtained sample changed into reddish brown when water was added. It was then observed that the color of the sample returned to green again when the sample was dried at a temperature of 100 C.°, that is, the color change was reversible.

Second Embodiment

A phosphorus porphyrin-methanol solution was obtained by dissolving 0.05 g of the phosphorus porphyrin complex (B) synthesized according to the same procedure as in the first embodiment in 500 ml of methanol. Then, 200 g of JIS A-type spherical silica gel (particle size: 1.70-4.00 mm) was prepared, and 84 ml of the phosphorus porphyrin-methanol solution was sprayed to the spherical silica gel. The spraying was performed carefully not to decrepitate the spherical silica gel due to a shock by adsorption heat. The silica gel after the spraying was dried at a temperature of 100 C.° and then left standing to cool down.

Subsequently, 84 ml of a 1 weight % calcium chloride solution was sprayed to the silica gel. The silica gel after the spraying was dried at a temperature of 100 C.° and then left standing to cool down to obtain a sample.

In the sample obtained according to the above procedure, an added amount of the phosphorus porphyrin complex (B) was 42 μg and an added amount of calcium chloride was 4.2 mg per 1 g of silica gel.

Then, a first moisture adsorption, i.e., a first hygroscopicity test, was conducted. Specifically, the obtained sample was exposed for 48 hours to monitor color changes thereof under each of the following conditions: at a relative humidity of 20%, at a relative humidity of 50% and at a relative humidity of 90% according to "JIS Z0701 4.1 Hygroscopicity Test". The results showed that the color changed to green at a relative humidity of 20%, to brownish green at a relative humidity of 50%, and to brown at a relative humidity of 90%. In other words, gradual changes in color were observed.

When redried at a temperature of 100 C.°, the sample returned to green. When a second moisture adsorption, i.e., a second hygroscopicity test, was conducted, gradual changes in color depending on the relative humidity were observed in the same manner as in the first hygroscopicity test. This proved that the sample had reversibility in the color change.

FIG. 1 shows an adsorption isotherm of the sample measured at the time of the first moisture adsorption and at the time of the second moisture adsorption after the sample was redried. In FIG. 1, adsorption isotherms of a blue gel (i.e., cobalt chloride impregnated silica gel) and JIS A-type silica gel, which was used as a support, are also indicated.

In terms of adsorption properties, the sample showed an adsorption isotherm comparable to representative physical properties of the blue gel, and thus was confirmed to have an equivalent adsorption ability to the blue gel. Also, since the redried sample showed substantially the same results, it was confirmed that deterioration by the redrying was not caused. This proved that the sample had substantially the same adsorption ability as the blue gel.

Third Embodiment

A phosphorus porphyrin-methanol solution was obtained by dissolving 0.05 g of the phosphorus porphyrin complex (B) synthesized according to the same procedure as in the first embodiment in 500 ml of methanol. Then, 10 ml of a 1 weight % calcium chloride solution was added to the phosphorus porphyrin-methanol solution to prepare a phosphorus porphyrin-calcium chloride-methanol solution.

200 g of JIS A-type spherical silica gel (particle size: 1.70-4.00 mm) was prepared, and 84 ml of the phosphorus porphyrin-calcium chloride-methanol solution was sprayed to the spherical silica gel. The spraying was performed carefully not to decrepitate the spherical silica gel due to a shock by adsorption heat. The silica gel after the spraying was dried at a temperature of 100 C.° and then left standing to cool down to obtain a sample.

In the sample obtained according to the above procedure, an added amount of the phosphorus porphyrin complex (B) was 41 μg and an added amount of calcium chloride was 84 μg per 1 g of the silica gel.

Then, the same first hygroscopicity test as in the second embodiment was conducted on the obtained sample. The same gradual changes in color as in the second embodiment were observed, that is, the color changed to green at a relative humidity of 20%, to brownish green at a relative humidity of 50%, and to brown at a relative humidity of 90%.

When redried at a temperature of 100 C.°, the sample returned to green. When a second hygroscopicity test was conducted, gradual changes in color depending on the relative humidity were observed in the same manner as in the first hygroscopicity test. This proved that the sample had reversibility in the color change.

Figure 2:
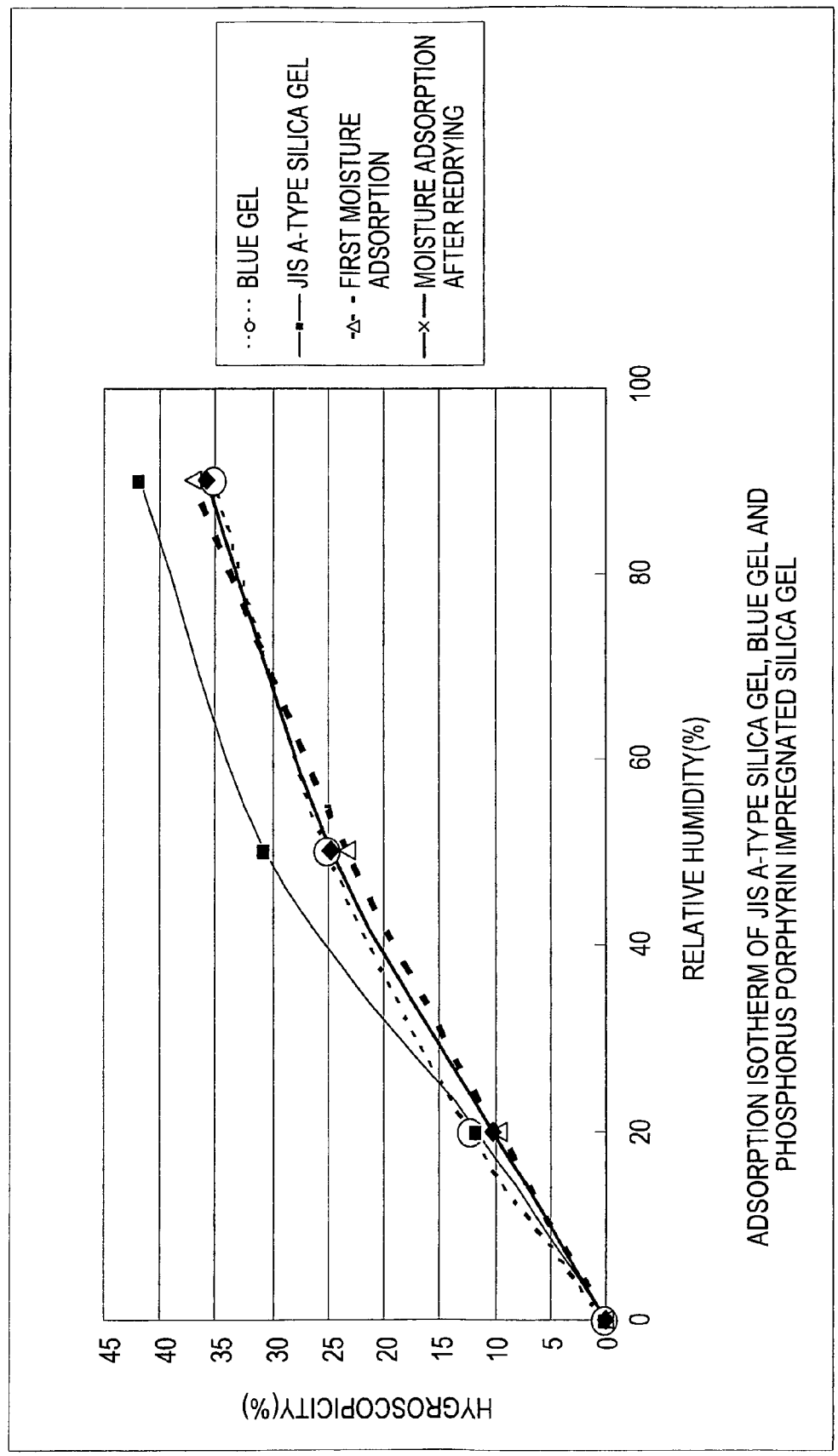
FIG. 2 is a graph showing an adsorption isotherm of a sample in a third embodiment.

FIG. 2 shows an adsorption isotherm of the sample measured at the time of the first moisture adsorption and at the time of the second moisture adsorption after the sample was redried. In FIG. 2, adsorption isotherms of a blue gel (i.e., cobalt chloride impregnated silica gel) and a JIS A-type silica gel, which was used as a support, are also indicated.

In terms of adsorption properties, the sample showed the same results as in the second embodiment, which proved that the sample had an equivalent adsorption ability to the blue gel and that deterioration by the redrying was not caused.

While calcium chloride was made to be supported after phosphorus porphyrin was made to be supported by the silica gel in the second embodiment, a mixture of phosphorus porphyrin and calcium chloride was made to be supported by the silica gel in the third embodiment. The fact that the both samples showed the same color changes depending on the humidity proved that the color changes were unaffected by the timing of adding calcium chloride.

Fourth Embodiment

A phosphorus porphyrin-methanol solution was obtained by dissolving 0.1 g of the phosphorus porphyrin complex (B) synthesized according to the same procedure as in the first embodiment in 200 ml of methanol. Then, 10 ml of a 1 weight % calcium chloride solution was added to the phosphorus porphyrin-methanol solution to prepare a phosphorus porphyrin-calcium chloride-methanol solution.

200 g of JIS A-type spherical silica gel (particle size: 1.70-4.00 mm) was soaked in the phosphorus porphyrin-calcium chloride-methanol solution overnight to impregnate the phosphorus porphyrin-calcium chloride-methanol solution into the silica gel. Subsequently, the silica gel was dried at a temperature of 100 C.° and then left standing to cool down to obtain a sample.

In the sample obtained according to the above procedure, an added amount of the phosphorus porphyrin complex (B) was 190 μg and an added amount of calcium chloride was 190 μg per 1 g of the silica gel.

Then, the same hygroscopicity test as in the second embodiment was conducted on the obtained sample. The results showed that the color changed to green at a relative humidity of 20%, to brown at a relative humidity of 50%, and to reddish brown at a relative humidity of 90%. In terms of adsorption properties, the results proved that the sample had substantially the same adsorption ability as a conventional cobalt chloride impregnated silica gel.

Figure 3:
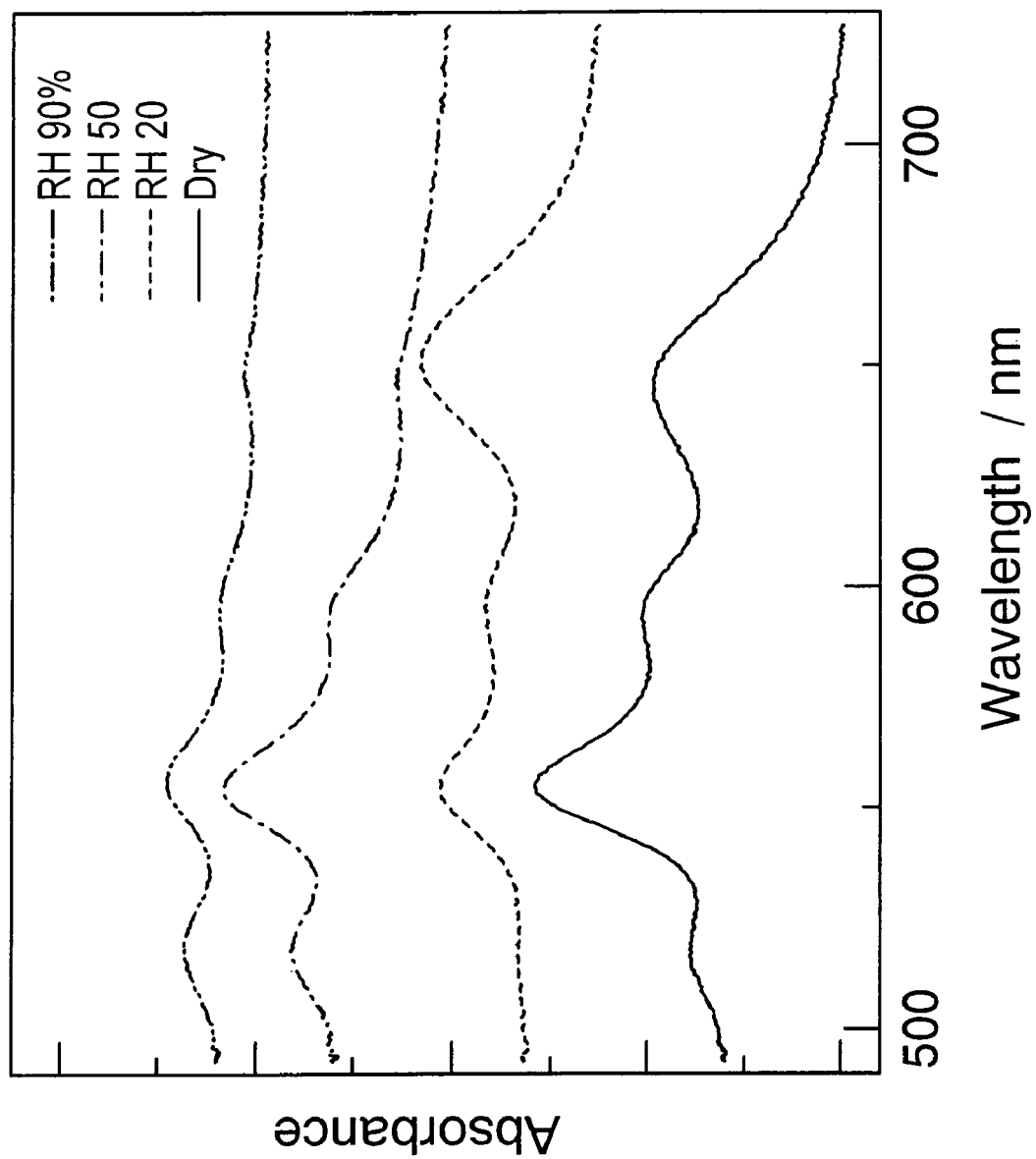
FIG. 3 is a graph showing an absorption spectrum of a sample in a fourth embodiment.

Absorption spectra were measured with respect to the sample before and after measuring the hygroscopicity (see measurement results in FIG. 3). As shown in FIG. 3, a peak around a wavelength of 560 nm is slightly shifted toward a longer wavelength side, and a peak around a wavelength of 650 nm disappears in accordance with absorption of moisture. The measurement results indicate that such spectra changes may cause the color changes of the sample.

Fifth Embodiment

A phosphorus porphyrin-methanol solution was obtained by dissolving 1.25 mg of the phosphorus porphyrin complex (A) obtained in the first embodiment in 15 ml of methanol. Then, 2 ml of a 50 weight % calcium chloride solution was added to the phosphorus porphyrin-methanol solution to prepare a phosphorus porphyrin-calcium chloride-methanol solution.

25 g of spherical silica gel (specific surface area: 600 m$^2$/g, pore volume: 0.6 ml/g, particle size: 1.70-4.00 mm) was prepared. 17 ml of the phosphorus porphyrin-calcium chloride-methanol solution was added to the spherical silica gel and the resulting mixture was stirred. The mixture was dried at a temperature of 100 C.° to obtain a sample.

In the sample obtained according to the above procedure, an added amount of the phosphorus porphyrin complex (A) was 50 μg and an added amount of calcium chloride was 40 mg per 1 g of the silica gel.

Then, the same first hygroscopicity test as in the second embodiment was conducted on the obtained sample. The same gradual changes in color as in the second embodiment were observed. In this case, the color changed to green at a relative humidity of 20%, to pinkish green at a relative humidity of 50%, and to pink at a relative humidity of 90%.

When redried at a temperature of 100 C.°, the sample returned to green. When a second hygroscopicity test was conducted, gradual changes in color depending on the relative humidity were observed in the same manner as in the first hygroscopicity test. This proved that the sample had reversibility in the color change.

Figure 4:
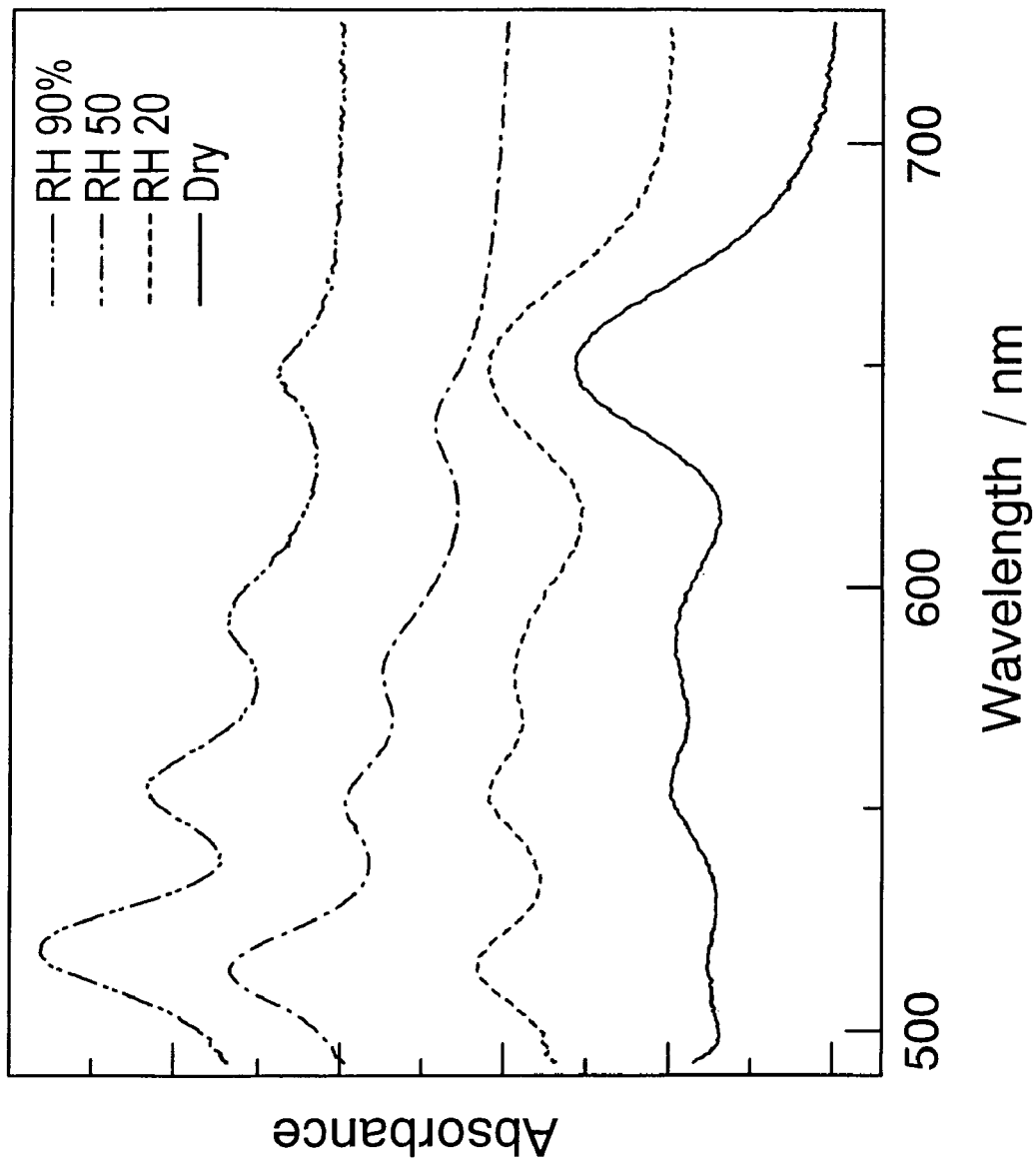
FIG. 4 is a graph showing an absorption spectrum of a sample in a fifth embodiment.

Absorption spectra were measured with respect to the sample before and after measuring the hygroscopicity (see measurement results in FIG. 4). As shown in FIG. 4, a peak around a wavelength of 515 nm appears, a peak around a wavelength of 560 nm is slightly shifted toward a longer wavelength side, and a peak around a wavelength of 650 nm is lowered in accordance with absorption of moisture. The measurement results indicate that such spectra changes may cause the color changes of the sample.

Sixth Embodiment

A sample was obtained under the same conditions and the procedure as in the fourth embodiment except for using calcium nitrate in place of calcium chloride used in the fourth embodiment.

Then, the same hygroscopicity test as in the fourth embodiment was conducted on the obtained sample, and changes in color in accordance with absorption of moisture were observed.

Seventh Embodiment

A sample was obtained under the same conditions and the procedure as in the fourth embodiment except for using magnesium chloride in place of calcium chloride used in the fourth embodiment.

Then, the same hygroscopicity test as in the fourth embodiment was conducted on the obtained sample, and changes in color in accordance with absorption of moisture were observed.

Eighth Embodiment

Samples were obtained under the same conditions and the procedure as in the fourth embodiment except for using ferrous chloride, ferric chloride, aluminum chloride (hexahydrate), lithium chloride, and potassium chloride, respectively, in place of calcium chloride used in the fourth embodiment.

Then, the same hygroscopicity test as in the fourth embodiment was conducted on each of the obtained samples, and changes in color in accordance with absorption of moisture were observed.

Ninth Embodiment

Samples were obtained under the same conditions and the procedure as in the fourth embodiment except for using ferrous sulfate, ferric sulfate, aluminum sulfate, lithium sulfate, and potassium sulfate, respectively, in place of chlorides used in the eighth embodiment.

Then, the same hygroscopicity test as in the fourth embodiment was conducted on each of the obtained samples, and changes in color in accordance with absorption of moisture were observed.

Tenth Embodiment

Samples were obtained under the same conditions and the procedure as in the fourth embodiment except for using ferrous nitrate, ferric nitrate, aluminum nitrate, lithium nitrate, and potassium nitrate, respectively, in place of chlorides used in the eighth embodiment.

Then, the same hygroscopicity test as in the fourth embodiment was conducted on each of the obtained samples, and changes in color in accordance with absorption of moisture were observed.

Eleventh Embodiment 20 ml of a 1 weight % calcium chloride solution was added to 20 g of silica gel (mean particle size: 1.70-4.00 mm). The resulting mixture was stirred and dried to obtain a silica gel previously impregnated with calcium chloride in pores (hereinafter referred to as the "calcium chloride impregnated silica gel"). 20 ml of phosphorus porphyrin-methanol solution (prepared by dissolving 0.01 g of the phosphorus porphyrin complex (B) synthesized according to the same procedure as in the first embodiment in 20 ml of methanol) was added to the calcium chloride impregnated silica gel. The resulting mixture was stirred and dried to obtain a sample.

Then, the same hygroscopicity test as in the fourth embodiment was conducted on the obtained sample, and changes in color in accordance with absorption of moisture were observed.

While the embodiments of the present invention have been described above, the present invention should not be limited to the above described embodiments, but may be practiced in various forms.

For example, while P (phosphorus) is exemplarily employed in the embodiments as the central element M of the complex indicated in the above general equation [I], the central element M of the complex may be selected from Mg, Al, Si, Ca, Sc, Ti, V, Cr, Mn, Fe, Co, Ni, Cu, Zn, Ga, Ge, As, Mo, Ru, Rh, Pd, Ag, Cd, In, Sn, Sb, W, Re, Pt, Au, Hg, Tl, Pb, and Bi. That is, as long as the central element M of the complex is selected from these elements, changes in color will be caused due to moisture adsorption or contact with water. It may, therefore, be possible to select the central element M from these elements considering purposes, production costs, etc.

While a spraying method and an impregnation method were used to make the porphyrin complex and the inorganic acid salt supported by the silica gel in the above embodiments, other methods may be employed.

While silica gels (e.g., JIS A-type silica gel) having specific physical properties are exemplarily employed as supports in the embodiments, there is no limitation to physical properties of silica gels. A silica gel having physical properties of, for example, a specific surface area of 10-800 $m^2/g$ and a pore volume of 0.2-2.0 ml/g may be used as a support.

Also, the support is not limited to silica gel. Specifically, another inorganic porous material may be impregnated with the porphyrin complex and the inorganic acid salt. Alternatively, it may be possible to constitute a moisture-adsorbing support by impregnating a support such as paper with a fluid composition containing silica gel or by coating such a fluid composition on a support, and make the porphyrin complex and the inorganic acid salt supported by the moisture-adsorbing support, depending on how to use a water detection indicator. Furthermore, a moisture-adsorbing paper may be used as a support even if the paper is not impregnated with an inorganic porous support such as silica gel.

While methanol is employed as a solvent of the porphyrin complex in the embodiments, it may be possible to use an organic solvent, e.g., toluene, xylene, acetone and isopropyl alcohol, or use such an organic solvent after being dissolved in a water soluble solvent and diluted with water.

While added amounts of the porphyrin complex and the inorganic acid salt are exemplarily specified in the embodiments, the added amounts may be optionally changed as long as the amounts will result in significant changes in color.

Furthermore, while the porphyrin complex based on tetra-phenyl porphyrin is exemplarily specified in the embodiments, hydroxy groups as axial ligands or four phenyl groups may be replaced by other functional groups.

Specifically, a hydroxy group as an axial ligand in tetra-phenyl porphyrin may be replaced preferably by an alkyl group which may be replaced by a phenyl group, a cycloalkyl group, a phenyl group which may have a substituent, or an acyl group which may have a substituent considering easiness in production, stability, etc. of the porphyrin complex. Examples of a substituent in "a phenyl group which may have a substituent, or an acyl group which may have a substituent" are an alkyl group, an alkoxy group, a carboxy group, a fluoro group, a chloro group, a bromo group, an iodo group, a hydroxy group, a cyano group, an amino group, a formyl group, a phenyl group, an acyl group, and a nitro group. However, a hydroxy group or a halogen is more preferable as the axial ligand to make the porphyrin complex more stabilized on a support having a hydroxy group, such as silica gel.

The four phenyl groups in tetra-phenyl porphyrin are preferably phenyl groups which may have substituents considering easiness in production, stability, etc. of the porphyrin complex. Specifically, the substituents which phenyl groups may have are, for example, an alkyl group, an alkoxy group, a carboxy group, a fluoro group, a chloro group, a bromo group, an iodo group, a hydroxy group, a cyano group, an amino group, a formyl group, a phenyl group, an acyl group, and a nitro group.

What is claimed is:
1. A water detection indicator comprising:
a water detection composition, including, as active components:
  a porphyrin complex; and
  at least one inorganic acid salt of a metal selected from a group consisting of alkali metals, alkaline earth metals, Al and Fe;
wherein the porphyrin complex is indicated by Formula I:

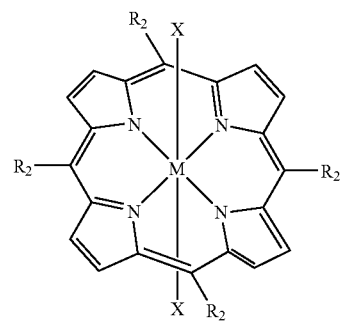

wherein M is P;
  X is selected from a group consisting of a halogen and OH; and
  R$_2$ is phenyl, and
the water detection composition is supported by a silica gel.

2. The water detection indicator according to claim 1, wherein the inorganic acid salt is a chloride of one of Ca and Mg.

* * * * *